United States Patent [19]

Szymaitis

[11] Patent Number: 5,664,582
[45] Date of Patent: Sep. 9, 1997

[54] METHOD FOR DETECTING, DISTINGUISHING AND COUNTING OBJECTS

[76] Inventor: Dennis W. Szymaitis, 1172 Harvard Rd., Pittsburgh, Pa. 15205

[21] Appl. No.: 519,771

[22] Filed: Aug. 28, 1995

Related U.S. Application Data

[63] Continuation-in-part of Ser. No. 176,769, Jan. 3, 1994, Pat. No. 5,456,718, which is a continuation-in-part of Ser. No. 977,336, Nov. 17, 1992, abandoned.

[51] Int. Cl.⁶ .................................................. A61B 19/00
[52] U.S. Cl. .......................... 128/898; 128/897; 128/899
[58] Field of Search ............................ 128/897, 898, 128/899

[56] References Cited

U.S. PATENT DOCUMENTS

| | | | |
|---|---|---|---|
| 2,190,431 | 2/1940 | Lewison | 128/156 |
| 2,698,270 | 12/1954 | Mesek | 154/93 |
| 3,577,136 | 5/1971 | Wolf | 340/280 |
| 3,587,583 | 6/1971 | Greenberg | 128/296 |
| 3,665,449 | 5/1972 | Elder et al. | 340/280 |
| 4,074,249 | 2/1978 | Minasy | 340/280 |
| 4,124,664 | 11/1978 | Maringer | 264/8 |
| 4,134,538 | 1/1979 | Lagarde et al. | 235/449 |
| 4,185,626 | 1/1980 | Jones et al. | 128/156 |
| 4,205,680 | 6/1980 | Marshall | 128/296 |
| 4,215,342 | 7/1980 | Horowitz | 340/572 |
| 4,290,993 | 9/1981 | Maringer | 264/164 |
| 4,298,862 | 11/1981 | Gregor et al. | 340/572 |
| 4,342,904 | 8/1982 | Onsager | 235/493 |
| 4,405,535 | 9/1983 | Raman et al. | 264/11 |
| 4,416,289 | 11/1983 | Bresler | 128/737 |
| 4,431,005 | 2/1984 | McCormick | 128/656 |
| 4,445,501 | 5/1984 | Bresler | 128/1.5 |
| 4,568,921 | 2/1986 | Pokalsky | 341/572 |
| 4,581,524 | 4/1986 | Hoekman et al. | 235/493 |
| 4,622,543 | 11/1986 | Anderson, III et al. | 340/572 |
| 4,626,311 | 12/1986 | Taylor | 156/308.2 |
| 4,769,631 | 9/1988 | Copeland | 340/551 |
| 4,857,891 | 8/1989 | Heltemes | 340/551 |
| 5,003,291 | 3/1991 | Strom-Olsen et al. | 340/551 |
| 5,015,992 | 5/1991 | Strom-Olsen et al. | 340/551 |
| 5,015,993 | 5/1991 | Strom-Olsen et al. | 340/551 |
| 5,027,886 | 7/1991 | Strom-Olsen et al. | 164/463 |
| 5,045,071 | 9/1991 | McCormick et al. | 604/280 |
| 5,057,095 | 10/1991 | Fabian | 604/362 |
| 5,079,006 | 1/1992 | Urquhart | 600/12 |
| 5,329,944 | 7/1994 | Fabian et al. | 128/899 |
| 5,456,718 | 10/1995 | Szymaitis | 623/11 |

Primary Examiner—Paul B. Prebilic
Attorney, Agent, or Firm—Buchanan Ingersoll, P.C.; Lynn J. Alstadt

[57] ABSTRACT

A method and apparatus for detecting, distinguishing and counting marked objects and particularly marked surgical objects having a marker made of a selected nonmagnetostrictive, soft magnetic material which will emit known specific selected high harmonic frequencies when exposed to an alternating electromagnetic field. That emission will cause a change in the alternating electromagnetic field which can be correlated to the presence of only the selected nonmagnetostrictive, soft magnetic material.

20 Claims, 4 Drawing Sheets

METHOD FOR DETECTING, DISTINGUISHING AND COUNTING OBJECTS

This is a continuation in part of my U.S. Pat. application Ser. No. 08/176,769 filed Jan. 3, 1994 now U.S. Pat. No. 5,456,718 which is a continuation in part of my U.S. patent application Ser. No. 07/977,336 filed Nov. 17, 1992 now abandoned.

BACKGROUND OF THE INVENTION

1. Field of the Invention

The invention relates to detecting, distinguishing and counting objects in an operating room using a detection device which responds to an alternating electromagnetic field.

2. Description of the Prior Art

Despite precautions, surgeons still occasionally leave surgical objects such as sponges and, less frequently, small surgical tools in their patients after an operation. Areas which are badly injured tend to have a great amount of blood which may cover the surgical objects, making the objects hard to locate. Also, objects may find their way under an organ. This is most likely to occur in surgical areas such as the abdomen which is large and has many organs.

The prior art discloses use of X-ray opaque material positioned on the surgical devices in order that after the surgery is completed and the wound is closed, an X-ray can be taken to insure that no surgical objects were left within the patient. Although this detection method is effective, it is cumbersome. Most operating rooms do not have X-ray machines. Hence, the patient must be taken to another room. There the patient often must be moved from his gurney to an X-ray table for X-rays to be taken. If a surgical object is detected after an X-ray has been taken, the patient must be returned to the operating room. Then, the cavity or incision must be reopened to remove the surgical object and then reclosed. This second surgery can cause a great deal of trauma to the patient, preventing optimum healing. Examples of surgical sponges which are marked by radiopaque material are disclosed in U.S. Pat. No. 2,190,432 to Lewison, U.S. Pat. No. 2,698,270 to Mesek, U.S. Pat. No. 4,185,626 to Jones et al., and U.S. Pat. No. 4,205,680 to Marshall.

Manual counting of the sponges and other surgical objects after the surgery is completed is also used to prevent those objects from being left in body cavities. This is not a foolproof method. Fatigue, poor handwriting, and misreading of numbers will occur during operations lasting 4 to 12 hours when dealing with badly damaged patients. Consequently, miscounts occur as a result of human error.

Surgical objects are counted not only to insure that no such objects are left in the human body, but also to prevent such objects from being inadvertently discarded. There have been instances where a surgical item costing several thousand dollars has been discarded with the surgical trash.

Presently, many operating rooms follow a practice of placing all used and soiled sponges, drains, packs and other objects in a holding container. At the end of the operation the container is emptied and the objects that had been contained therein are counted. Blood on the discarded objects may contain infectious disease viruses. Therefore, each time a soiled surgical object is handled there is a risk of accidental self inoculation. Consequently it is desirable to minimize the handling of such objects, not handle each discarded object twice as in this current practice.

Because of the risks of infection and in an effort to minimize human error, the art has developed several methods of marking objects for automatic detection. Many of those methods rely upon markers which respond to a magnetic or electromagnetic field.

Greenberg in U.S. Pat. No. 3,587,583 attempts to overcome the problems of leaving surgical objects within the human body. He proposes to mark the surgical object with a permanently magnetized material. A surgeon performs an operation in the normal manner. Before closing the incision the surgeon probes for the presence of a surgical object with a magnetic field detector means which generates an electric signal which is modified in the presence of a magnetic field. If the marked object is present, the magnetic field of the magnetic marker is sensed by the magnetic field detector means, which modifies the electric signal. Yet, an operating room has many types of equipment which generate permanent magnetic fields. The presence of those fields can activate the magnetic field detector means, giving false detection. Because of its unreliability in an operating room, Greenberg's device is not a practical solution to the problem.

In U.S. Pat. No. 5,057,095, Fabian proposes to mark surgical instruments with a marker adapted to produce identifying signal characteristics when exposed to an alternating magnetic field. He discloses three types of resonant markers that are able to resonate at a certain preselected frequency. The first marker is a magnetomechanical device comprised of a permanent magnet overlaying a magnetostrictive metal strip in a plastic housing. The magnetostrictive strip vibrates when the marker is exposed to an alternating electromagnetic field, and its resonance is detected when the frequency of the applied field reaches a predetermined value. However, such devices are very sensitive to pressure and stress, which will inhibit them. Since a body cavity is under some pressure and the marker may be stressed during surgery, this type of marker is not reliable for use as a marker for surgical objects. The second proposed type is an electromechanical circuit comprised of an air coil, with or without a ferrite core, and a resonant structure such as a piezoelectric crystal. As the first type, this type of marker can be adversely affected by pressure and stress because its principle of detection relies on a electromechanical resonance; therefore, a piezoelectric crystal type marker is also unsatisfactory. The third type of marker proposed by Fabian is an electromagnetic LCR circuit. This type of marker can be either built out of discreet components or made of a flexible printed circuit. In the former case, this unit is expensive to build and bulky, and it is impractical for surgical sponges. In the latter case, due to its high electrical resonance frequency this type of marker can be adversely affected by the presence of metal objects and conductive media. Because the human body is conductive, this type of marker is also impractical for surgical sponges. Consequently, none of the markers proposed by Fabian, nor the Greenberg marker, has been available on the market.

In U.S. Pat. No. 5,045,071, McCormick teaches about the use of magnetic materials for accurately locating the position of a catheter which has been inserted into a blood vessel. At column 9, lines 12–16, the patent cross references U.S. Pat. Nos. 4,416,289, 4,431,005 and 4,445,501 for an explanation of the general method of detection. At column 5, lines 41–52, the '005 patent explains that a distortion of the magnetic field indicates the presence of the catheter. Thus, the McCormick patent teaches that merely a change in the magnetic field is a sufficient indicator of the position of the marked object. However, McCormick's measurements can be affected by the presence of other nearby magnetic and conductive materials. Hence, McCormick's technique can and likely will provide "false positives" as to the presence or the position of the marked object.

Thus, there is a need for a marking method and apparatus for detecting and counting surgical objects within the human body and elsewhere in an operating theater utilizing a material that can be readily identified before the patient leaves the operating suite. The method and marker must not give false positives or otherwise be ineffective in the presence of magnetic and electromagnetic fields of the type commonly produced in the operating room. Such a marker and method may also be useful outside the operating room in environments where objects must be counted or detected and in which magnetic or electromagnetic fields are present.

3. Techniques for Detecting Electromagnetic Material

There are different ways of providing and detecting what we can call generically an "electromagnetic marker." The cited prior art references all use materials which respond to an electromagnetic field. In order for a material to respond to an electromagnetic field and therefore to create "detectable changes" of the electromagnetic field, a material has to have at least one of the physical properties of electrical conductivity, moderate to high magnetic permeability, and magnetostriction (in general associated with moderate magnetic permeability). Moderate magnetic permeability is defined as a permeability comprised of between 5,000 and 20,000 and high magnetic permeability as a permeability above 20,000. In each case, the response to the electromagnetic field and, therefore, the creation of "detectable changes" of the electromagnetic field are heavily dependent upon the geometry and size of the marker. In addition, the response to the electromagnetic field depends upon the intensity and frequency of the electromagnetic field.

In general, a magnetic material subject to an electromagnetic field of known and fixed frequency $f_o$ responds to the applied electromagnetic field by creating "changes" of the intensity of the applied field and by creating harmonics of the frequency $f_o$. If the material is electrically conductive, it responds by creating not only "changes" of the intensity of the applied field but also "changes" of the phase of the field. In addition, if the material is magnetostrictive, the electromagnetic field creates strains or stress in the material, and the material responds to it by creating a frequency-dependent "change" of the intensity and of the phase of the applied field. Therefore, there are three methods of detection. First, one can simply look for a change of intensity and/or phase in an applied magnetic field, a method which can only be used for detection of the position of an object at a distance comparable to the size of the object. McCormick uses this method. Second, one could look for the frequency of the applied field to reach a predetermined value that is the electromechnical resonance frequency of the marker. Fabian discloses a magnetomechanical device which uses this technique. Finally, one could look for particular harmonics generated by a material in the presence of an applied magnetic field. This method has never been used in a medical environment. Indeed, the teaching of Heltemes in U.S. Pat. No. 4,857,891 indicates that the art has generally failed to recognize that "open-strip" markers made of selected nonmagnetostrictive materials which generate specific harmonic frequencies upon application of a unidirectional electromagnetic field can be used to identify the presence of particular articles.

Heltemes discloses a Magnetic Marker for Electronic Article Surveillance Systems having multiple filaments randomly dispersed in a sheet-like substrate so as to be substantially parallel to the plane thereof. "The filaments are selected of low coercive force, high permeability material, and the random orientation results in certain filaments intersecting with them being magnetically coupled to other filaments to thereby collect and concentrate lines of flux associated with an applied field of an EAS system into filaments parallel to the field."

To take advantage of a high magnetic permeability material a marker has to be elongated (fiber, long strip, with an aspect ratio length/square root or cross-sectional area of a least 200). Heltemes complies only partially to this requirement, but randomly distributes the fibers. In this respect Heltemes defeats this purpose because the applied electromagnetic field has to be parallel to the magnetic fibers to generate a high enough level of high harmonics to be recognized as marker specific. Moreover, Heltemes' marker is not very well suited for generating high harmonics. Consequently, Heltemes, like others in the prior art, failed to recognize that markers could be created for detection of surgical objects which generate specific, detectable, selected harmonic frequencies.

SUMMARY OF THE INVENTION

I provide a marker for a surgical object or other object which marker responds to the presence of an alternating electromagnetic field. That response is detectable as discrete pulses of radio frequencies. The marker is comprised of at least one elongated member made of nonmagnetostrictive, soft magnetic material encapsulated in biocompatible material. Preferably, the magnetic material is an amorphous metal. However, crystalline materials can be used if the encapsulation material has a high flexibility and plasticity.

I further provide a method for detecting marked objects which includes marking the object with my marker and exposing the marked object to an alternating electromagnetic field. The marker will emit energy in the form of known frequencies when it is exposed to the alternating electromagnetic field. Detection is made using a pulse detection technique similar to that used in magnetic resonance imaging (MRI), a common and safe diagnostic procedure. A patient or area that may contain a marker object is exposed to an alternating electromagnetic field of about 3–40 Oe (oersteds) for a specific time. This field will cause the elongated member to become magnetized and consequently to generate harmonics of the frequency of the applied alternating electromagnetic field. A detector placed nearby will detect the reflected waveform from the marker as sharp signal peaks at the specific frequency of the applied alternating electromagnetic field.

My marker is particularly useful for surgical sponges. However, other surgical tools (e.g., forceps, scalpel), plastic or rubber/polymer surgical implement or equipment used during surgery (e.g., plastic drain, suction tubes), and implants (e.g., artificial veins, artificial arteries, knee replacement) may also be marked. The marker can also be used on small tools or parts that may become lost within a machine or other piece of equipment during manufacture, inspection, repair or use. Examples of such equipment include computers, MRI machines, CAT scan units, conveyor systems and similar production line and packaging line systems.

When the object is a surgical sponge, the marker can be woven into the sponge. When the surgical object is a surgical tool such as forceps, the marker is placed on the tool by an adhesive means.

In the case where the object is an implant, the method of detecting the object can be used as a diagnosis of past medical history of implants. Each type of implant can contain a specific material or combination of materials that emits a specific signal that corresponds to that object. Thus, if the patient is incoherent, the doctor can diagnose the patient's past medical history of implants. The use of markers which emit different signals on different types of objects is applicable to any situation in which more than one type of marked object can be present and there is a need or desire to know the type of object that is detected.

When the marker is used in an operating room, I prefer to perform the excitation and detection steps prior to the closing of the surgical incision. I can thereby prevent the usual infection that would go along with leaving the surgical object within a body and the trauma which corresponds with reopening the incision to remove the surgical object.

Other details, objects and advantages of the invention will become apparent as the following description of a present preferred embodiment thereof and a present preferred method of practicing the same proceeds.

BRIEF DESCRIPTION OF THE DRAWINGS

In the accompanying drawings I have shown a present preferred embodiment of the invention in which.

DETAILED DESCRIPTION OF THE PREFERRED EMBODIMENTS

Figure 1:
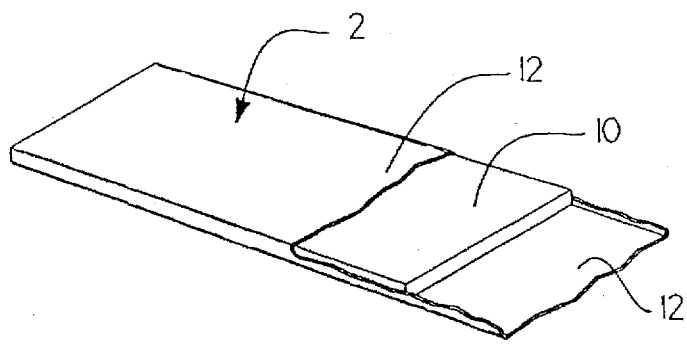
FIG. 1 is a perspective view partially cut away of a present preferred marker.

As shown in FIG. 1, my marker 2 is comprised of an elongated body 10 of soft magnetic material which is nonmagnetostrictive. It is characteristic of many ferromagnetic materials that even the slightest applied mechanical strain tends to cold work the material and degrade its permeability and other magnetic properties. Nonmagnetostrictive magnetic materials are insensitive to strain; they have the required magnetic properties for my marker but they are also sensitive to work hardening. Amorphous materials are very difficult to cold work. Preferably, the material of my marker is a nonmagnetostrictive amorphous material with very soft magnetic properties. It should have high magnetic permeability, a low coercive field, and induction saturation should be as high as possible. One suitable material is sold by Allied under the trademark "Metglas." The composition of the alloy is recited in U.S. Pat. No. 4,298,862 to Gregor et al. Thus, for example, Allied compositions identified as types 2826MB® or 2705M may be preferably used. Another suitable amorphous material is Vitrovac 6025Z soft magnetic amorphous alloy with zero magnetostriction sold by Vacuumschmelze GmbH of Hanau, Germany. Although the marker body could be any dimension and shape, I prefer to make the elongated body 10 as a ribbon or a strip or a set of parallel ribbons, strips, fibers or filaments. The elongated geometry of these members allows me to take advantage of the high magnetic permeability of the materials. Preferably, the elongated members will have an aspect ratio (length/square root of cross-sectional area) of at least 200. Such a sufficiently large value for the aspect ratio will assure generation of a detectable signal according to the teachings of U.S. Pat. No. 3,665,449. If the direction of an applied electromagnetic field is essentially parallel to the marker, and the intensity of the applied electromagnetic field is greater than a minimum field or threshold, then the marker will generate high harmonics of the frequency of the applied electromagnetic field. That is, the marker will emit a spectrum of harmonics whose intensity decreases slowly with the order of the harmonics in the spectrum. In particular, the 9th or the 11th harmonics should be detectable. Higher harmonics could also be detectable. I prefer the ribbon 10 to have a width less than 2 mm, preferably about 0.5 mm, a thickness ranging between 0.01 to 0.03 mm and a length of about 5 to 7 cm. Body 10 could be longer or shorter, but preferably not shorter than 3 mm.

The width and thickness of the ribbon 10 can be selected to obtain flexibility so that when the marker is attached to an object such as a surgical sponge, it will not adversely affect the flexibility of the object. I prefer to encapsulate the elongated body in a polymeric material that is compatible with the human body. Suitable coating materials are nylon and delrin plastic. The coating 12 prevents the body from oxidizing or reacting with body fluids and covers any sharp edges or corners of the ribbon 10.

In order to maximize the ratio of the length to the square root of the cross-sectional area, it has been found desirable that the material be as thin and as narrow as practical, depending upon off-setting production cost considerations. It is evident that fibers possess the required geometry. The metallic fiber which I prefer to use can be made in accordance with the teachings of U.S. Pat. Nos. 5,003,291, 5,015,992, 5,015,993 and 5,027,886 by Strom-Olsen and Rudkowski. These fibers are nonmagnetostrictive, amorphous magnetic materials with very high magnetic permeability. Typically, the diameter of such fibers ranges between 0.01 and 0.04 mm.

Figure 2:
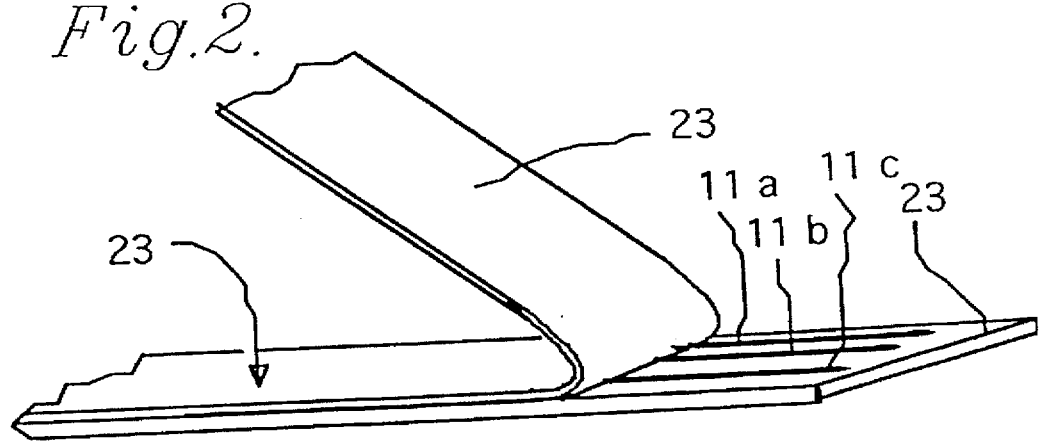
FIG. 2 is a perspective view partially cut away of a second preferred marker.

I further provide marking means in the form of a flexible marker made of fiber laminated between two layers of polymeric materials. In order for detection to occur, one to approximately ten fibers should be placed parallel to each other, and each fiber should be approximately 1 to 3 inches in length. Such a multiple fiber marker assembly is shown in FIG. 2. As shown, the marker of this invention comprises two layers 23 in the form of a web or ribbon of polymeric materials. I provide a plurality of fibers 11a, 11b and 11c arranged parallel to each other and secured between the two layers 23 by adhesion or lamination means. As mentioned earlier and for the same reasons, I prefer to make use of a polymeric material that is compatible with the human body.

However, a marker made of a ribbon or fiber should be less than the length or the width of the surgical object or not so long that it would require significant bending or multiple folding for attachment to the object to be marked. When one is outside this preferred range, a response signal from the marker will be less characteristic and therefore more difficult to identify.

Although my markers would be X-ray detectable, one could impregnate the coating or layers with an X-ray opaque material such as a barium compound to improve detectability. Another possibility is to use an X-ray opaque coating material which is currently being used on medical products. Use of such material not only improves the detectability of the marker, but should also reduce the time needed to obtain government and hospital approval of use of the marker.

One could also use nonmagnetostrictive crystalline magnetic materials such as Permalloy alloy for the marker body 10. If a crystalline material is used, the cover layer of polymeric material should be designed to minimize the transfer of mechanical stress induced upon bending or folding the marker.

Figure 3:
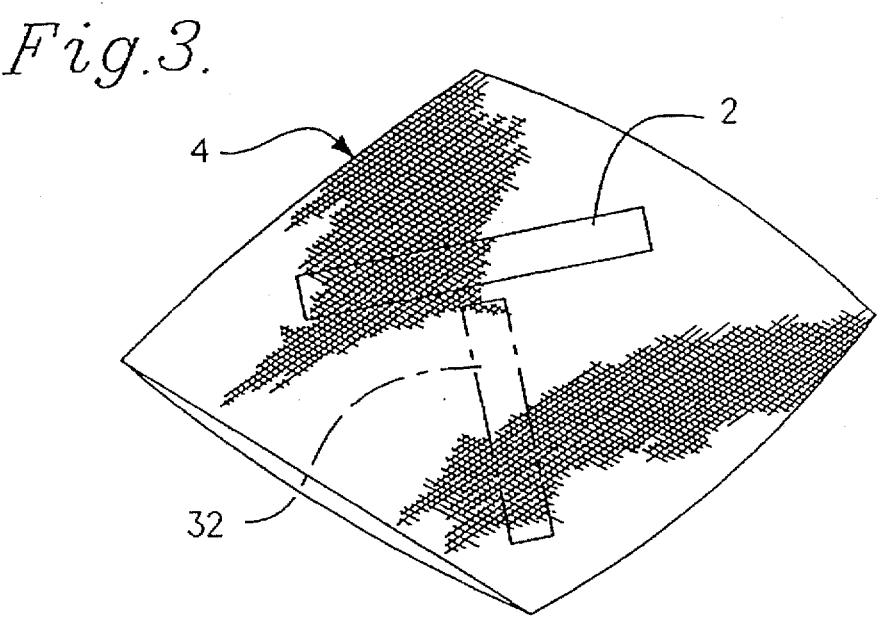
FIG. 3 is a perspective view of a surgical sponge having one and optionally two markers woven through the sponge.

The surgical sponge 4 shown in FIG. 3 is a gauze sponge having a marker 2 woven throughout the sponge. It is understood that other means of attachment or securing the marker 2 to the surgical sponge 4 can be used. The marker can be connected to the sponge by means of pressure, heat, adhesive or the like.

Figure 5:
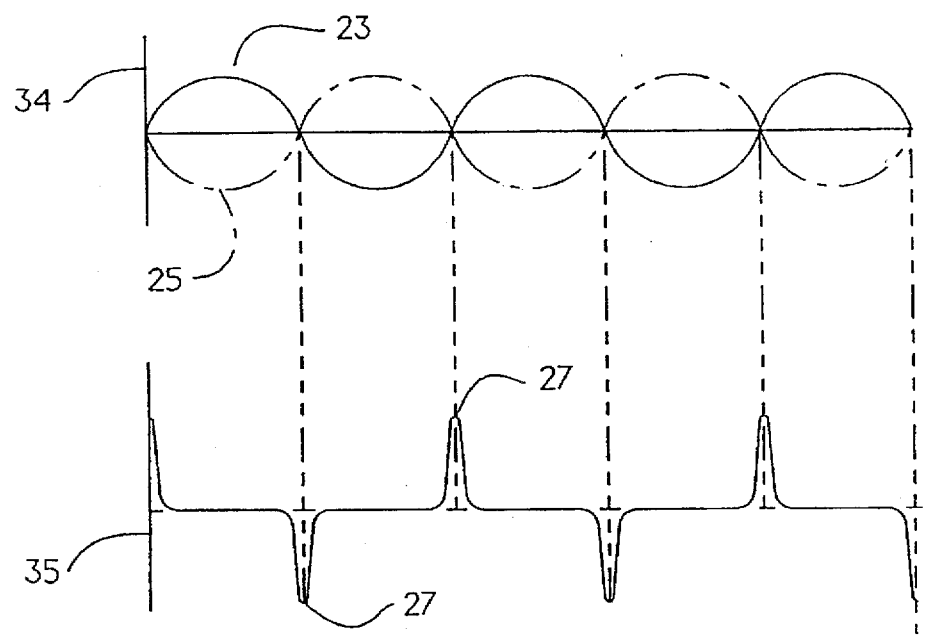
FIG. 5 is a graph of responses of a detector in the presence of my marker.

Either the marker of FIG. 1 or the marker of FIG. 2 could be used. I prefer to use markers which are shorter than a length or a diagonal of the sponge to avoid bending or folding. Optionally, I may use a second marker 32, shown in chainline, positioned at a right angle to the first marker 2. This configuration assures that the sponge will be detected regardless of its orientation with respect to the detector. One could use more than two markers on an object. But, as the number of markers increases, the response of the marked object to a detector will likely be less distinctive. Therefore, I prefer to use one or two markers positioned as in FIG. 3. This arrangement provides a distinctive response such as shown in FIG. 5.

It is relatively easy to detect an object marked with my marker. Once the surgery procedure is completed, the surgeon exposes the surgical cavity to an alternating electromagnetic field, using the detection system. Preferably, the patient will be on a nonmagnetic gurney or examination table. A very low electromagnetic field of approximately 3 to 40 Oe is all that is required. Such a field is relatively easy to establish and will not harm the patient or the equipment which is normally found in an operating room. If desired, one may use as little as 1.50 Oe and as much as 60 Oe or higher. However, it is normally not practical to exceed 10 Oe because such high fields would interfere with other equipment present in an operating room. This magnetic field will cause the marker body attached to any surgical objects in the surgical cavity to emit specific harmonic frequencies of the frequency of the applied electromagnetic field corresponding to the selected marker material. That emission will cause a change in the alternating electromagnetic field, which change can be correlated to the presence of only the selected nonmagnetostrictive, soft magnetic marker material. The detection system can be designed to measure all changes in the applied electromagnetic field and then look for the specific change which would be caused by the presence of the marker. Alternatively, the detection system could be designed to measure only a change or changes of the type which would be caused by the presence of the selected marker material or materials.

A number of techniques and variety of devices could be used to detect the presence of the magnetized marker body attached to a surgical object left in the patient. Those techniques and devices should be apparent to those skilled in the art. The detection system circuitry with which the marker 2 is associated can be any system capable of (1) generating within an interrogation zone an incident alternating electromagnetic field, and (2) detecting magnetic field variations at selected harmonic frequencies of the frequency of the applied electromagnetic field produced in the vicinity of the interrogation zone by the presence of the marker therewithin. Such systems typically include means for transmitting a varying electrical current from an oscillator and amplifier through conductive coils that form a frame antenna capable of developing an alternating magnetic field.

Figure 4:
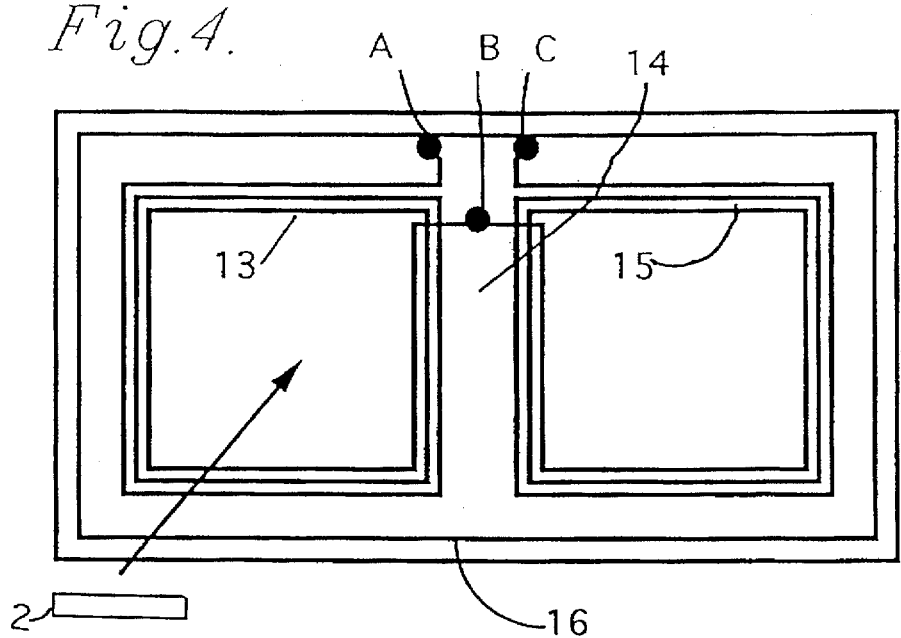
FIG. 4 is a diagram of a detector of my marker.

A fairly simple detector is illustrated in FIG. 4. A flat search coil 14 has a first section 13 wound in a clockwise direction from points A to B and a second section 15 with the same number of windings running in a counter-clockwise direction from points B to C. A frame inductor antenna 16 is placed near the search coil. If an AC current is passed through the inductor antenna, an alternating magnetic field will be created. That field will induce a voltage through the search coil. One can detect the voltage from points A to B and plot it on coordinates 34 in FIG. 5 as a sine wave 23. The voltage from points B to C can be plotted as a sine wave 25, 180 degrees out of phase from sine wave 25. If the two waves are plotted simultaneously, they will cancel each other and yield a straight line over the time-axis. In the event a magnetized marker moves within the interrogation zone of coil 14, it will change the AC magnetic field received by the coil 14 and modify waves 23 and 25. For a single marker, that modification can be seen as a series of peaks 27 also shown in FIG. 5 on coordinates 35. The points along the time-axis where peaks occur depend upon the size and composition of the marker. If too many markers are used, the peaks would flatten and approach a sine wave. Therefore, I prefer not to use more than two markers, preferably oriented as in FIG. 3. The marker produces peaks at particular points along the x-axis. Thus, the detector looks for a response at those intervals. Only if a response occurs at the chosen points is a detection made. It is possible that equipment in the operating room, such as CRTs, will generate electromagnetic fields which will cause a detector response. However, the chances that such interference will produce peaks at the selected intervals is small. Hence, false detections are remote possibilities, and they can be eliminated by predetecting and electronically canceling the signals of such equipment.

Figure 6:
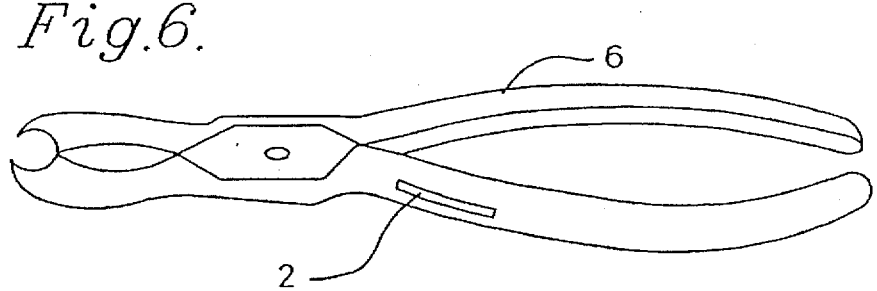
FIG. 6 is a perspective view of a pair of forceps having a marker positioned on the exterior handle surface.

My markers can be used in other surgical equipment such as forceps, scalpels and hemostats. FIG. 6 shows a pair of forceps 6 which have a marker positioned along the handle. My markers can also be used to mark surgical implants. Hence, a physician could learn about an implant in the patient's past medical history using my detection method. The area under suspicion of an implant will be excited at a specific frequency. If an implant exists in that area, it will emit energy over a specific spectrum of frequency which corresponds to the specific implant material. For this diagnostic process to work, a standard must be used for all implants. Standard material should be used for each specific implant differing the material from one implant to another. In that event, the response will identify the specific implant.

Figure 7:
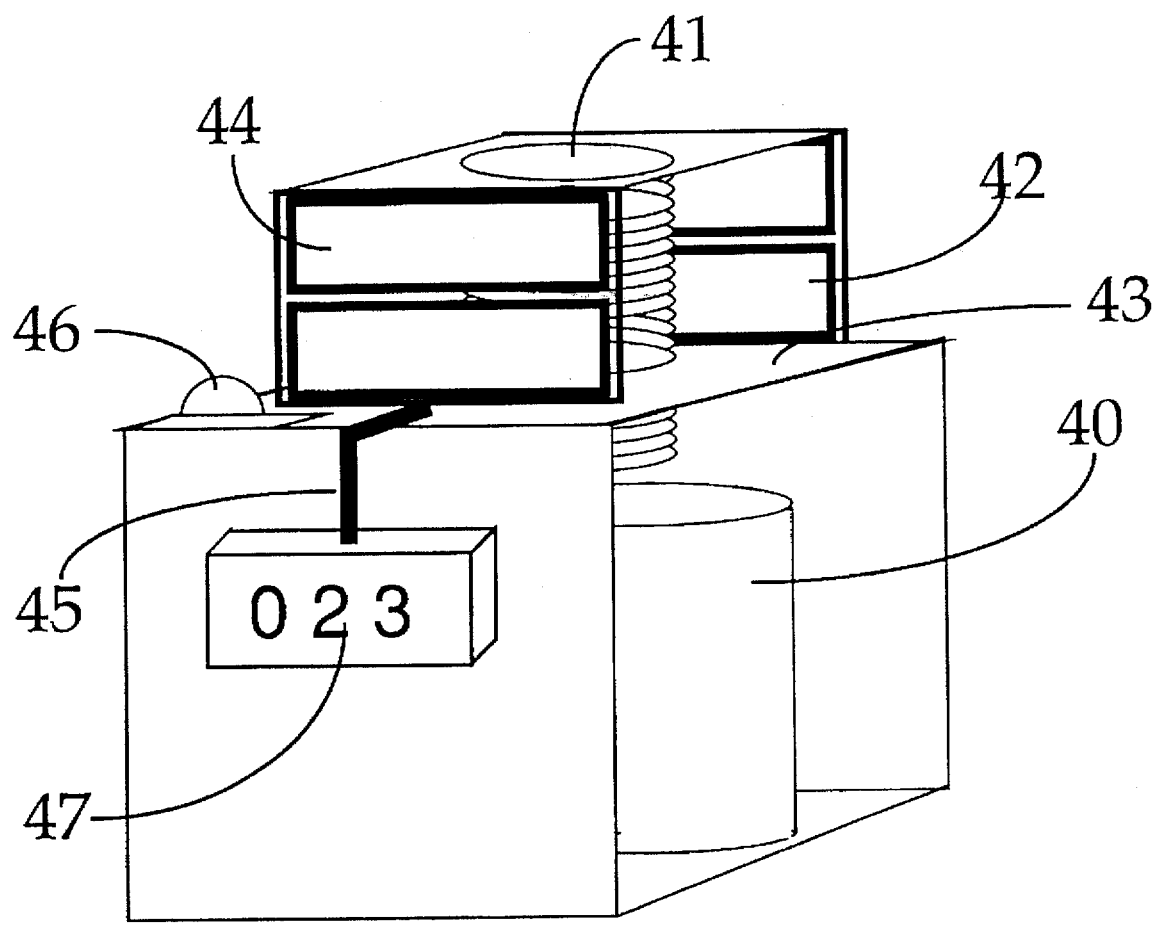
FIG. 7 is a perspective view of a container having mounted thereon a detector with associated components for detecting, distinguishing and counting marked objects as they are placed into the container.

Marked objects can be detected and counted at the time of disposal using a waste container of the type shown in FIG. 7. A detector 42 is placed on the top 43 of the waste container near opening 1. Another detector 44 is placed on the container 40, opposite the first detector 42. At least one of the detectors includes an electromagnetic field generator. Whenever a marked object is dropped into the container 40 the marker on the object will emit a signal that is detected by the detector. The detector will then emit a corresponding signal to a control system to indicate that a marked object has been discarded. Preferably, the control system is attached to or within the container as indicated by chain line box 45. The control system causes a display 47 to show the number of marked items that have been discarded. Although not shown, the control system could be connected to an external computer which utilizes or stores the number of discarded, marked items. This information could be used for patient billing or other purposes. The container 40 may have a warning light 46 or LED display which is illuminated whenever an object having a particular marker is detected. If surgical sponges which are to be discarded have a marker that evokes one response and other objects are marked with a marker that prompts a different response, the control system can be designed to illuminate the light only when marked objects which are not to be discarded pass the detector. The detectors 42 and 44 that are placed on the container 40, could also be used in other locations, such as at a doorway or disposal chute, to detect and count the passage of marked objects.

Figure 8:
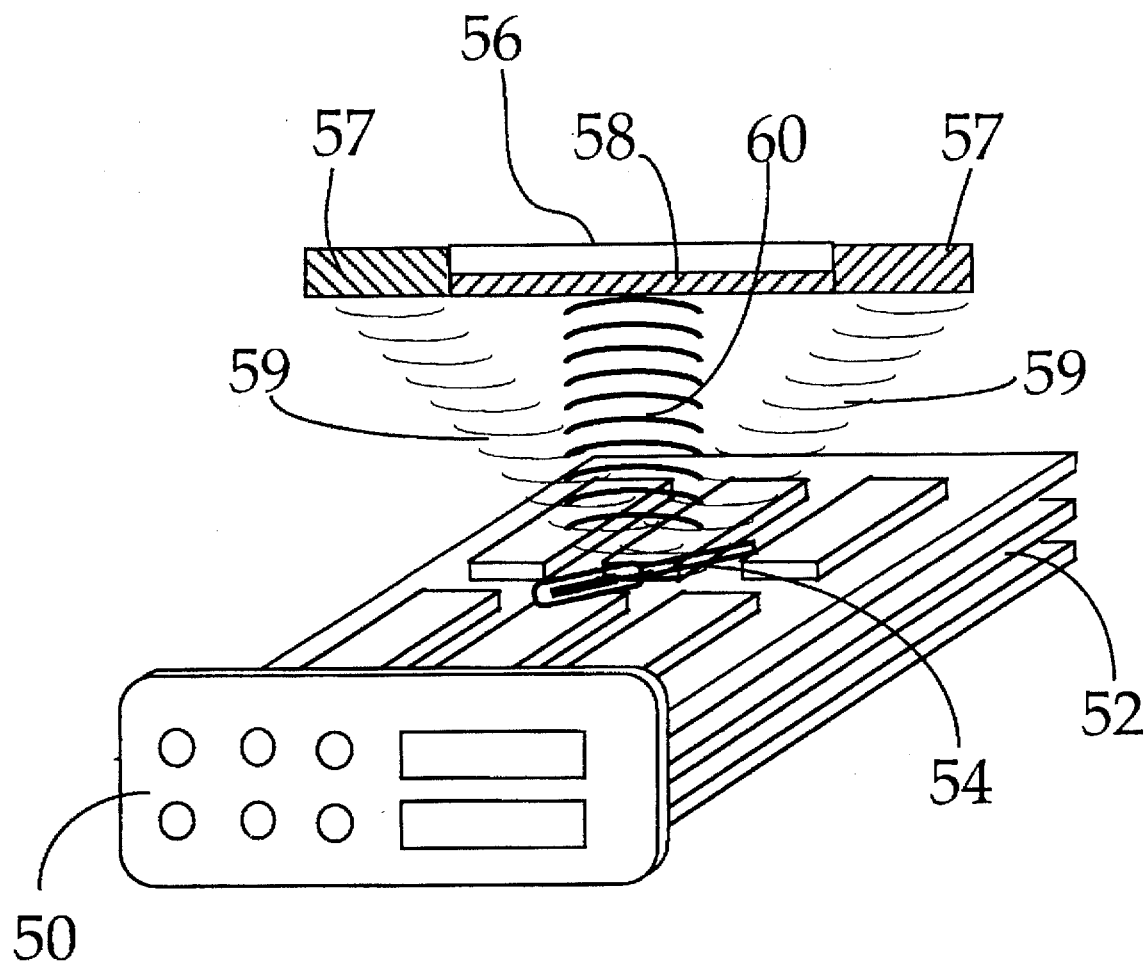
FIG. 8 is a perspective view of a probe which contains a detector with associated components and which is positioned above an open personal computer containing a lost marked object therein that is being detected.

The present marker and method can be used in non-medical environments. In FIG. 8 there is shown an electronic device 50, the cover of which has been removed exposing a stack of circuit boards 52. A marked tool 54 has been left inside the device during assembly or repair. A probe 56 is placed above the device. The probe contains a frame inductor antenna 57 for generating the electromagnetic field and a flat search coil detection unit 58. If an AC current is passed through the inductor antenna it creates an alternating electromagnetic field 59 which causes the marked object to respond in a way that modifies the field in a manner 60 that is detected by detection unit 58.

In FIGS. 7 and 8 I have shown certain preferred orientations and geometries of the elements that generate the electromagnetic field and detect the harmonics produced by the marker. Those skilled in the art will recognize that there are many other possible embodiments. For example, a frame inductor antenna can be placed opposite a search coil. Two frame inductor antennas could be placed at right angles to two search coil detectors. The electromagnetic field could be created by two frame inductor antennas placed near a search coil detector. Other types of coils could be used, either for generating the electromagnetic field or for detecting the signal from a marker.

I have shown and described the present preferred embodiments of the invention. It is to be distinctly understood that the invention is not limited thereto, but may be otherwise variously embodied within the scope of the following claims.

I claim:

1. A method for detecting at least one object comprising:
   a) attaching to each of the at least one object a marker comprised of at least one elongated body of a selected nonmagnetostrictive, soft magnetic material, each said at least one elongated body being parallel to any other elongated body such that said marker will emit a spectrum of harmonics which includes detectable high order harmonics, and which will emit at least one known specific intensity of harmonic frequencies when exposed to an alternating electromagnetic field thereby causing a change in the alternating electromagnetic field which change can be correlated to the presence of only the selected nonmagnetostrictive, soft magnetic material;
   b) exposing the at least one object to an alternating electromagnetic field thereby causing a change in the alternating electromagnetic field; and
   c) detecting with a detector the change in the alternating electromagnetic field thereby indicating that the at least one object has been detected.

2. The method of claim 1 wherein the object is a surgical sponge.

3. The method of claim 2 wherein the marker is woven into the sponge.

4. The method of claim 1 wherein the marker comprises a soft magnetic amorphous material.

5. The method of claim 1 wherein the marker comprises a ribbon of soft magnetic amorphous material.

6. The method of claim 1 also comprising the step of encapsulating the marker in a biocompatible coating.

7. The method of claim 6 wherein the coating is radio-paque.

8. The method of claim 1 wherein the marker comprises at least one fiber of soft magnetic amorphous material.

9. The method of claim 1 wherein the marker comprises a soft magnetic crystalline material.

10. The method of claim 1 wherein the marker comprises a ribbon of soft magnetic crystalline material.

11. The method of claim 1 wherein the marker comprises at least one fiber of soft magnetic crystalline material.

12. The method of claim 1 wherein the at least one elongated body has an aspect ratio of at least 200.

13. The method of claim 1 wherein the alternating electromagnetic field is generated by a generator placed near the detector.

14. The method of claim 13 wherein the generator and the detector are attached to a container.

15. The method of claim 13 wherein the generator and the detector are contained within a probe.

16. The method of claim 1 wherein a plurality of objects are marked and each object is separately exposed to the alternating electromagnetic field and also comprising the step of counting the objects which are exposed to the alternating electromagnetic field.

17. The method of claim 16 also comprising the step of displaying a number corresponding to how many objects have been detected.

18. The method of claim 1 wherein the method is performed in an environment in which electromagnetic fields originating from at least one source other than the generator are present.

19. The method of claim 1 wherein the environment is an operating room.

20. The method of claim 1 wherein the at least one object is comprised of:
   a) a first set of objects each marked with a marker which will emit at least one known first specific intensity of harmonic frequencies when exposed to an alternating electromagnetic field; and
   b) a second set of objects each marked with a marker which will emit at least one known second specific intensity of harmonic frequencies when exposed to an alternating electromagnetic field, which second specific intensity of harmonic frequencies is different from the at least one known first specific intensity of harmonic frequencies.

* * * * *